(12) United States Patent
Previn et al.

(10) Patent No.: US 8,496,649 B2
(45) Date of Patent: Jul. 30, 2013

(54) RETINAL REJUVENATION LASER

(75) Inventors: Victor Previn, Adelaide (AU); Malcolm Plunkett, Adelaide (AU)

(73) Assignee: Ellex R&D Pty Ltd, Adelaide (AU)

( * ) Notice: Subject to any disclaimer, the term of this patent is extended or adjusted under 35 U.S.C. 154(b) by 778 days.

(21) Appl. No.: 12/600,393

(22) PCT Filed: May 29, 2008

(86) PCT No.: PCT/AU2008/000763
§ 371 (c)(1),
(2), (4) Date: Nov. 16, 2009

(87) PCT Pub. No.: WO2008/144828
PCT Pub. Date: Dec. 4, 2008

(65) Prior Publication Data
US 2010/0152716 A1    Jun. 17, 2010

(30) Foreign Application Priority Data
May 30, 2007   (AU) ................................ 2007902889

(51) Int. Cl.
*A61B 18/18*    (2006.01)
*A61F 9/008*    (2006.01)

(52) U.S. Cl.
CPC ............. *A61F 9/008* (2013.01); *A61F 9/00814* (2013.01)
USPC ............................................................. 606/4

(58) Field of Classification Search
CPC .............................. A61F 9/008; A61F 9/00814
USPC ....................................... 606/4, 5, 6; 128/898
See application file for complete search history.

(56) References Cited

U.S. PATENT DOCUMENTS

| | | | |
|---|---|---|---|
| 5,066,293 A | 11/1991 | Furumoto | |
| 5,302,259 A | 4/1994 | Birngruber | |
| 5,549,596 A | 8/1996 | Latina | |
| 5,756,541 A | 5/1998 | Strong et al. | |

(Continued)

FOREIGN PATENT DOCUMENTS

| | | | |
|---|---|---|---|
| WO | 0191661 A1 | | 12/2001 |
| WO | WO 01/91661 | * | 12/2001 |

(Continued)

OTHER PUBLICATIONS

"PCT International Search Report dated Aug. 15, 2008 for PCT/AU2008/000763, from which the instant application is based," 4 pgs.

(Continued)

*Primary Examiner* — Huy K Mai
(74) *Attorney, Agent, or Firm* — Fredrikson & Byron, P.A.

(57) ABSTRACT

A laser treatment device for use in retinal regeneration. The laser treatment device includes a laser module that delivers a pulse or sequence of pulses having a pulse duration in the range of 50 ps to 500 ns, a wavelength in the range 500 nm to 900 nm, and a pulse energy in the range 100 µJ to 10 mJ. The laser treatment device also includes a uniform irradiance module that modifies an output beam profile of the laser module to produce a uniform treatment effect and a beam delivery and viewing module that delivers the laser pulse or pulses to the retina with a radiant exposure in the range of 8 mJ/cm$^2$ to 8000 mJ/cm$^2$ per pulse.

18 Claims, 5 Drawing Sheets

U.S. PATENT DOCUMENTS

| | | | |
|---|---|---|---|
| 6,514,241 | B1 | 2/2003 | Hsia |
| 6,540,391 | B2 | 4/2003 | Lanzetta |
| 6,671,043 | B1 | 12/2003 | Huettman |
| 6,733,490 | B1 | 5/2004 | Falsini |
| 7,115,120 | B2 | 10/2006 | Lin |
| 2003/0179344 | A1 | 9/2003 | Van De Velde |
| 2004/0039378 | A1 | 2/2004 | Lin |
| 2004/0133190 | A1 | 7/2004 | Hobart |
| 2004/0215175 | A1* | 10/2004 | Feklistov et al. ............... 606/4 |
| 2005/0027288 | A1* | 2/2005 | Oyagi et al. ................. 606/16 |
| 2005/0048044 | A1 | 3/2005 | Schwartz et al. |
| 2006/0111697 | A1 | 5/2006 | Brinkmann et al. |

FOREIGN PATENT DOCUMENTS

| | | |
|---|---|---|
| WO | 02083041 A1 | 10/2002 |
| WO | 03101325 A1 | 12/2003 |
| WO | 2004026099 A2 | 4/2004 |
| WO | 2004027487 A1 | 4/2004 |
| WO | 2006021040 A2 | 3/2006 |
| WO | 2008049164 A1 | 5/2008 |

OTHER PUBLICATIONS

"PCT International Preliminary Report on Patentability dated Nov. 28, 2008 for PCT/AU2008/000763, from which the instant application is based," 8 pgs.

Roider, J., "Spatial confinement of photocoagulation effects using high repetition rate laser pulses," Conference on Lasers and Electro-Optics, 1990, Ahaheim, CA, vol. 7, pp. 168-169.

Ahir, A. et al., "Expression of Metalloproteinases from Human Retinal Pigment Epithelial Cells and Their Effects on the Hydraulic Conductivity of Bruch's Membrane," Investigative Ophthalmology & Visual Science, Feb. 2002, vol. 43, No. 2, pp. 458-465.

Roider, J. et al., "Subthreshold (retinal pigment epithelium) photocoagulation in macular diseases: a pilot study," Br J Ophthalmol. Jan. 2000:84(1): pp. 40-47.

Guo, L et al., "Age-Dependent Variation in Metalloproteinase Activity of Isolated Human Bruch's Membrane and Choroid," Investigative Ophthalmology & Visual Science, Oct. 1999, vol. 40, No. 11, pp. 2676-2682.

Moore, D. et al., "Age-Related Variation in the Hydraulic Conductivity of Bruch's Membrane," Investigative Ophthalmology & Visual Science, Jun. 1995, vol. 36, No. 7, pp. 1290-1297.

Starita, C. et al., "Localization of the Site of Major Resistance to Fluid Transport in Bruch's Membrane," Investigative Ophthalmology & Visual Science, Mar. 1997, vol. 38, No. 3, pp. 762-767.

Anderson, R. Rox et al., "Selective Photothermolysis: Precise Microsurgery by Selective Absorption of Pulsed Radiation," Science, Apr. 1983, vol. 220, pp. 524-527.

Starita, C. et al., "Decreasing hydraulic conductivity of Bruch's membrane, relevance to photoreceptor survival and lipofuscinoses," American Journal of Medical Genetics, 1995, 57(2): pp. 235-237.

Starita, C. et al., "Hydrodynamics of ageing Bruch's membrane; implications for macular disease," Experimental Eye Research, 1996, 62(5), pp. 565-571.

Marshall J. et al., "Aging and Bruch's membrane," Marmor MF ed. The Retinal Pigment Epithelium; Function and Disease, New York, Oxford University Press, pp. 669-692.

Hussain, A.A. et al., "Age-related alterations in the diffusional transport of amino acids across the human Bruch'schoroid complex," Journal of the Optical Society of America, A., Optics, Image Science, & Vision, 2002, 19(1), pp. 166-172.

Moorman, C. et al., "Clinical applications of the MicroPulse diode laser," Eye 13:145-150 (1999).

Roider, J. et al., "Subthreshold (retinal pigment epithelium) photocoagulation in macular diseases: a pilot study," J. Ophthalmol. 84:40-47 (2000).

Roider, J. et al., "Response of th eRetinal Pigment Epithelium to Selective Photocoagulation," Arch Ophthalmol—vol. 110, Dec. 1992, pp. 1786-1792.

Hussain, A.A. et al., "Transport Characteristics of Ageing Human Bruch's Membrane: Implications for Age-Related Macular Degeneration (AMD)," Chapter IV, Focus on Macular Degeneration Research, (Editor O.R. loseliani), ISBN 1-59033-878-7, Nova Science Publishers, Inc. NY (2004), pp. 59-103.

"PCT International Search Report dated Nov. 14, 2007 for PCT/AU2007/001622," 3 pgs.

"PCT International Preliminary Report on Patentability dated May 26, 2008 for PCT/AU2007/001622," 5 pgs.

* cited by examiner

RETINAL REJUVENATION LASER

RELATED APPLICATIONS

This application claims priority to International Application No. PCT/AU2008/000763 filed May 29, 2008, and to Australian Application No. 2007902889 filed May 30, 2007, the teachings of which are incorporated herein by reference.

FIELD OF THE INVENTION

This invention relates to a laser treatment device useful for improving the function of the retina of the human eye. This invention may be beneficially used in the treatment of eye diseases, such as early Age-related Macular Degeneration (AMD) in which the function of Bruch's membrane has become impaired as part of a disease pathogenesis, or the treatment of degradation related to aging.

BACKGROUND TO THE INVENTION

The light sensing and signaling processes of the human retina require a high level of support in terms of energy supply and waste removal to ensure optimal functionality. A monolayer of epithelial cells, known as the retinal pigmented epithelium (RPE) separates the light sensing and signaling processes from the blood supply of the choroid and it controls many bi-directional support functions. The RPE cells are attached to a basement membrane, known as Bruch's membrane, which is a thin extra-cellular matrix of collagen layers which act as a semi-permeable barrier between the RPE cells and blood vessels of the choroid. The work of Marshall, Hussain, Guo and Ahir, [Expression of Matalloproteinases from human retinal pigment epithelial cells and their effects on the hydraulic conductivity of Bruch's Membrane, Invest Ophthalmol Vis Sci. 2002 February;43(2):458-65] has shown that degradation of the transport functions of Bruch's membrane is a major contributor to loss or decline in visual function with normal aging or a more rapid decline due to diseases such as age-related macular degeneration (AMD). Although these transport functions begin to degrade from birth, serious vision loss may not occur until later in life when the RPE/Bruch's membrane/choroid complex degrades to a point at which it can no longer sustain the neuro-retina, resulting in atrophy of the neuro-retina or stress induced responses such as choroidal new vessel (CNV) growth.

Although changes in diet and environment have been recommended to reduce the rate of age related loss of visual acuity, no direct treatment for the retina exists, and almost all current treatments for AMD are focused on treating late stage complications such as CNV's. Current treatments for CNV's include photo-dynamic therapy (PDT) (as described in U.S. Pat. No. 5,756,541 assigned to QLT Phototherapeutics Inc) where a photosensitive drug is administered intravenously and then activated by a light source which is directed at the CNV, and intra-vitreal injections of drugs which inhibit the growth factors which promote new blood vessel growth (anti-VEGF).

Lasers have been used for many years to treat retinal disorders, predominately using their ability to coagulate tissue. The degree of laser energy absorption in retinal layers and structures is highly dependant on the wavelength used and one of the major absorbing chromophores within the retina is the melanin which pigments the RPE cells. Although the current retinal lasers use wavelengths that are strongly absorbed by the melanin of the RPE cells, the duration of the laser pulses which are currently used allows time for thermal diffusion from the RPE cells to adjacent structures and is particularly damaging to the neuro-retina resulting in permanent loss of visual function at the treatment site. Roider, Norman, Michaud, Thomas, Flotte and Birngruber [Response of the Retinal Pigment Epithelium to Selective Photocoagulation Arch Ophthalmology Vol 110, December 1992] describe that short duration laser pulses can be used to contain the energy within the RPE cells and prevent neuro-retinal damage, using a technique known as selective retinal therapy (SRT). SRT has been applied to a number of late stage retinal diseases with the aim of producing a therapeutic benefit by initiating a wound healing response at the level of the RPE, but with limited success, and the reason why a beneficial effect can be obtained in this way has not been explained.

The SRT method is well described in United Stated patent application 20040039378 by Lin in which a laser scanning device is used to provide very short irradiance times. While this patent describes the requirement for nanosecond duration exposures it is difficult to achieve the required radiant exposure level using the scanning method described.

OBJECT OF THE INVENTION

It is an object of this invention to provide a laser device to improve the function of the retina of the human eye.

Further objects will be evident from the following description.

DISCLOSURE OF THE INVENTION

In one form, although it need not be the only or indeed the broadest form, the invention resides in a laser treatment device for improving the function of the retina of the human eye comprising:
 a laser module producing a laser pulse or sequence of laser pulses each having:
  a pulse duration in the range of 50 ps to 500 ns,
  a wavelength in the range 500 nm to 900 nm; and
  a pulse energy in the range 10 µJ to 10 mJ;
 a uniform irradiance module that modifies an output beam profile of the laser module to produce a uniform treatment effect; and
 a beam delivery and viewing module that delivers the laser pulse or pulses to the retina with a radiant exposure in the range of 8 mJ/cm$^2$ to 8000 mJ/cm$^2$ per pulse.

Preferably the pulse duration is around 3 ns. The wavelength is suitably about 532 nm.

The radiant exposure is preferably in the range 20 mJ/cm$^2$ to 300 mJ/cm$^2$ per pulse.

The laser system is suitable for performing the method of retinal rejuvenation described in our co-pending international patent application number PCT/AU2007/001622.

BRIEF DETAILS OF THE DRAWINGS

To assist in understanding the invention preferred embodiments will now be described with reference to the following figures in which.

DETAILED DESCRIPTION OF THE DRAWINGS

In describing different embodiments of the present invention common reference numerals are used to describe like features.

Figure 1:
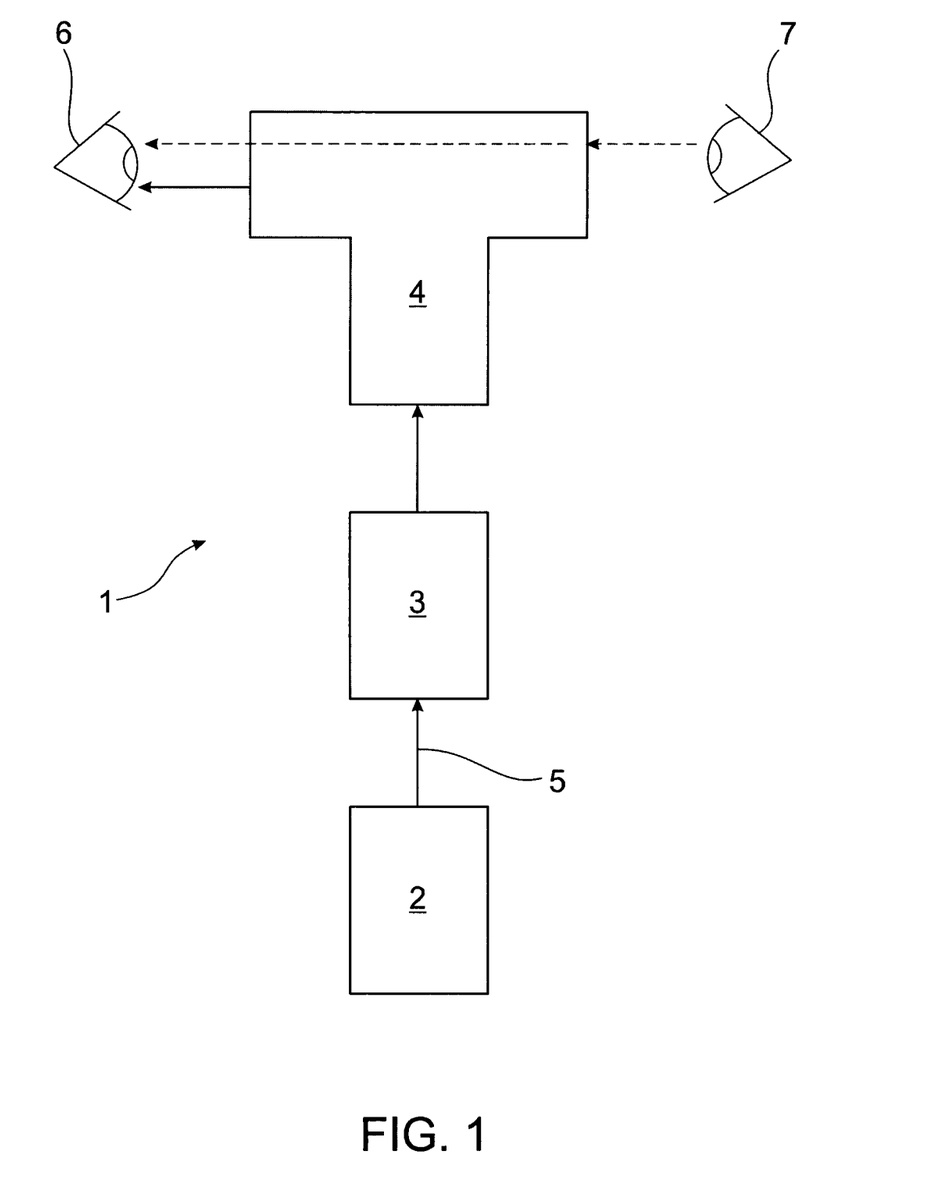
FIG. 1 is a block diagram of retinal rejuvenation laser.

Referring to FIG. 1 there is shown a block diagram of a retinal rejuvenation laser 1. The retinal rejuvenation laser 1 consists of a laser module 2 (described in more detail by reference to FIG. 2), a uniform irradiance module 3 (described in more detail with reference to FIG. 3), and a beam delivery and viewing module 4 (described in more detail with reference to FIG. 4). A laser beam 5 is generated by the laser module 2, manipulated for uniform irradiance by the uniform irradiance module 3 and directed to the eye 6 of a patient by the beam delivery and viewing module 4. The beam delivery and viewing module 4 incorporates a coincident viewing path for an operator 7.

Figure 2:
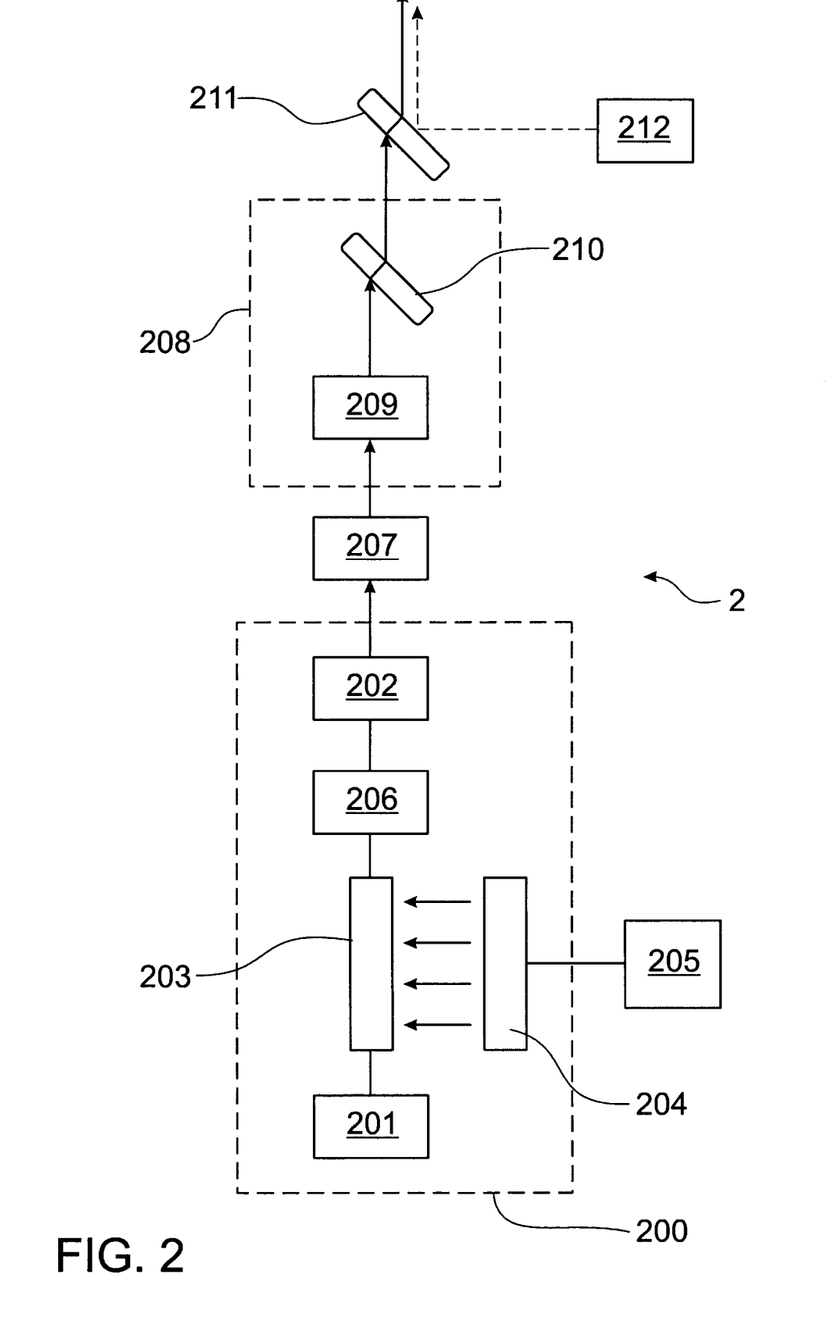
FIG. 2 is a block diagram of a laser module of the retinal rejuvenation laser of FIG. 1.

Referring now to FIG. 2, the preferred embodiment of the retinal rejuvenation laser 1 utilises a Q-switched flashlamp-pumped Nd:YAG laser producing nominally 1064 nm laser pulses. The laser cavity 200 is of conventional design having a 100% reflecting end mirror 201 and a partial reflecting output coupler 202. The laser rod 203 is excited by a flashlamp 204 that is energized by a high voltage power supply 205. A passive Q-switch 206 allows the cavity energy to be delivered as very short, high energy pulses. The laser output is converted to about 532 nm by a suitable frequency doubling crystal 207.

It will be appreciated that the specific wavelength of the laser output is determined by the laser medium and the optical arrangement. In a preferred embodiment the laser output is nominally 532 nm but the actual wavelength may not be exactly 532 nm.

Although a flashlamp pumped Nd:YAG laser is the preferred embodiment for the laser cavity the invention is not limited to this particular cavity design. Any laser cavity capable of producing pulses in the 50 ps to 500 ns range with a wavelength between about 500 nm and about 900 nm and pulse energy of around 10 □J to 10 mJ will be suitable. This includes other solid stated materials such as Er:YAG, Nd:YLF and Er:YLF. Other elements may also be varied. For instance, an active Q-switch may be used instead of a passive Q-switch.

The beam is directed to an optical attenuator 208 formed from a half wave plate 209 and polarizing optic 210. The optical attenuator allows fine control of the energy delivered from the laser module 2 by rotation of the half-wave plate 209. The laser module 2 also includes a beam combining optic 211 that combines the output from an aiming laser 212 into the same path as the laser module output (so that the treatment laser beam and the aiming laser beam are co-axial).

Figure 3:
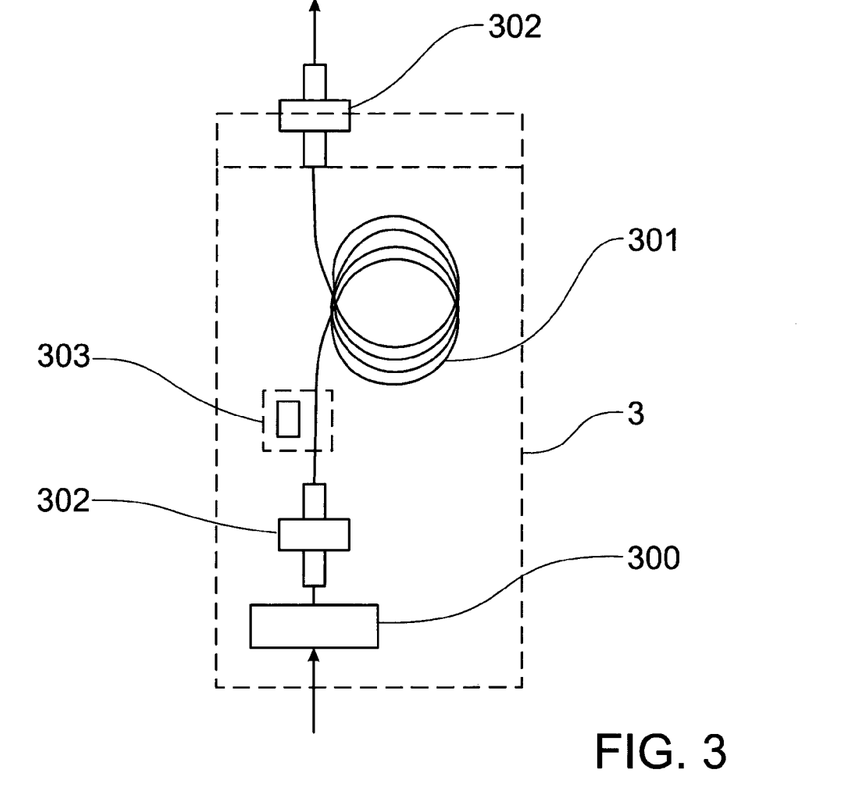
FIG. 3 is a block diagram of a uniform irradiance module of the retinal rejuvenation laser of FIG. 1.

The treatment laser beam output from the laser module 2 has a non-uniform and slightly variable energy distribution profile. If this was directly used to irradiate a target treatment zone some areas would receive lower radiant intensity while others would receive higher radiant energy. This is demonstrated below with reference to FIG. 5 and FIG. 6. To address this problem the treatment laser beam and aiming laser beam are directed to the uniform irradiance module 3. The uniform irradiance module 3 includes a fiber focus lens 300 that focuses the treatment laser and aiming laser beams into an optical fiber 301. Each end of the optical fibre 301 is terminated in a movable fitting 302 that facilitates accurate alignment.

When laser light is directed through an optical fibre, interference between propagation modes can result in a granular spatial distribution of the laser energy at the output which is referred to as speckle. By passing the output of the pulsed laser through an optical fiber as shown in FIG. 3 the structure of the energy distribution profile going into the fiber will be lost due to multiple internal reflections along the length of the optical fiber, resulting in a speckle profile at the fiber output. A single pulse such as this can be used for treatment with some areas between the peaks of the speckle pattern receiving low radiant intensity, resulting in a uniform but patchy treatment effect.

However, because the laser has some variability in the energy distribution profile, by producing another pulse which can be directed to the same target treatment zone a different speckle pattern will be produced by the optical fiber. Because of the random nature of the speckle patterns produced by each laser pulse, many of the peaks within the speckle pattern of the second pulse will occur in areas where low irradiance occurred on the first pulse, resulting in improved coverage of the target treatment zone. Subsequent laser pulses directed to the same target treatment zone will further improve the coverage, with successive pulses producing statistically less improvement as the coverage approaches 100%.

By selecting the number of laser pulses with speckle pattern which are delivered it is therefore possible to produce a uniform treatment effect but with a selected coverage of the target treatment zone. The granularity of the laser speckle can also be varied by using optical fibres with different optical characteristics, such as numerical aperture. Selection of coverage of the target treatment zone and speckle granularity, in conjunction with the laser treatment spot size, may be used to optimize the wound healing response and therapeutic benefit. Preferably the number of pulses is within the range of 1 to 5 and the numerical aperture of the fibre is within the range of 0.1 to 0.35.

In a further embodiment of the invention, where the pulsed laser has a non-uniform but stable energy distribution profile, or to improve the probability of different speckle patterns being produced by each pulse, the device can include an optical fiber vibrator 303. The vibrator 303 can be in the form of a small motor mechanically coupled to the fiber as shown in FIG. 3, with an offset shaft load to cause the vibration or alternatively a piezo-electric transducer may be used in the same way. A small amount of continually variable lateral or angular displacement is induced into the fiber by the vibrating means which alters the internal reflections within the fiber and continually alters the speckle pattern. The pulse repetition rate must be low enough to allow sufficient movement of the fiber, by the vibrating means, to produce a randomly different speckle pattern. In the case of a flashlamp pumped laser cavity this pulse repetition rate may be achieved by charging multiple discharge capacitors and then discharging them individually through the flashlamp by means of an electronic switching and control system. For example, a motor with an offset shaft load running asynchronously at 10,000 RPM would produce one shaft rotation approximately every 6 ms, so a pulse repetition rate of about 33 Hz or less would ensure a different speckle pattern with each pulse.

Vibration of the optical fiber has the added advantage of greatly reducing the speckle pattern of a co-axial aiming laser, traveling through the same optical fiber as the treatment laser beam, thereby improving usability.

Figure 4:
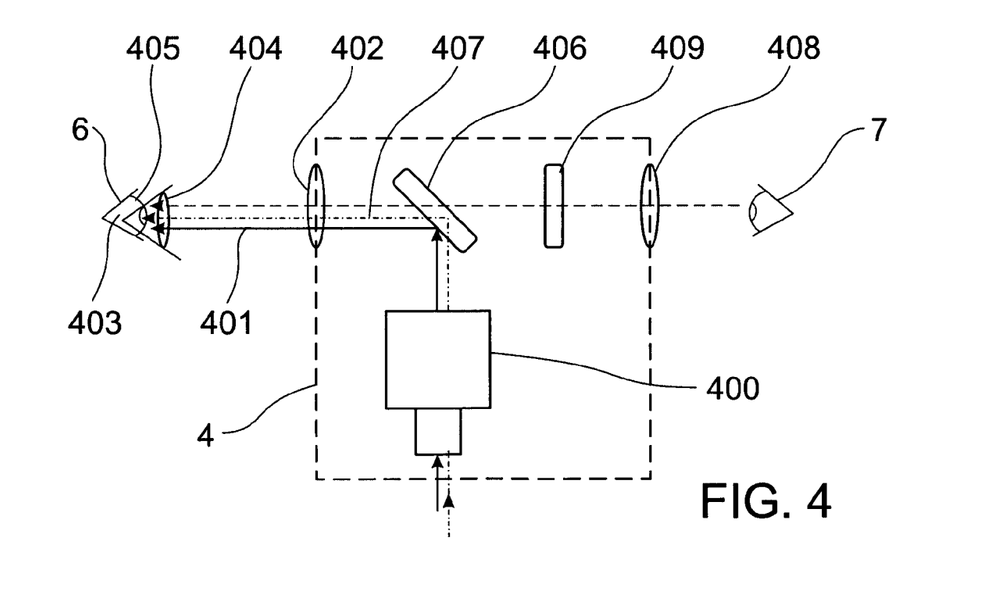
FIG. 4 is a block diagram of a beam delivery and viewing module of the retinal rejuvenation laser of FIG. 1.

The output from the uniform irradiance module 3 is directed to the beam delivery and viewing module 4, shown in FIG. 4. The beam delivery and viewing module 4 consists of an optical zoom module 400 that sizes and focuses the treatment laser beam 401 through an objective lens 402 to the retina 403 of the eye 6 of a patient. A contact lens 404 on the cornea 405 of the eye 6 is conventionally used to counteract the cornea and lens of the eye in the optical path. A binocular viewing microscope 408 is commonly used. A folding mirror 406 is reflective at the wavelength of the treatment laser beam 401 and the aiming laser beam 407 and is situated between the binocular viewing paths. A safety filter 409 protects the user from back scattered laser radiation.

The optical zoom module 400 can be preset to image the optical fibre output onto the retina via the contact lens, or it can be made adjustable to allow treatment spot size selection.

Figure 5:
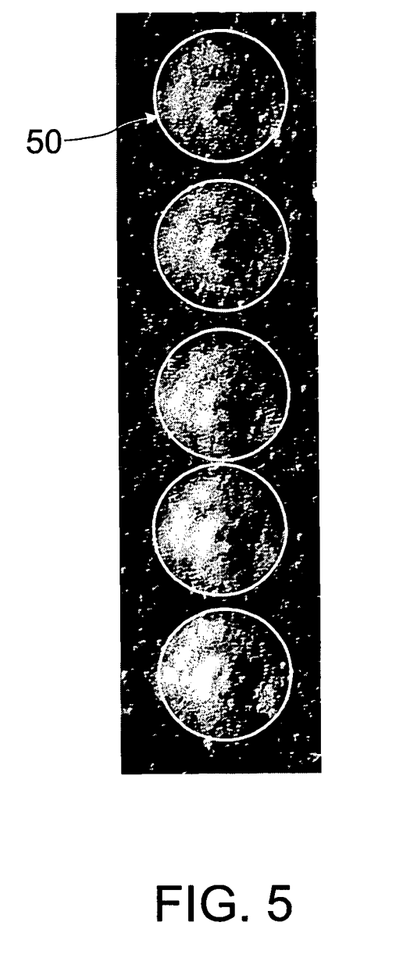
FIG. 5 shows the energy distribution profile of laser pulses applied to an aluminium target.

As mentioned above, the output from the laser module 2 is a beam with a non-uniform energy distribution profile. This is shown in FIG. 5. The energy distribution profile of a 3 ns passively Q-switched, flashlamp pumped Nd:YAG laser pulse is applied to a painted aluminium target to display the non-uniform profile. The target treatment zone is indicated by a circle 50. The damage caused at the target zone for one, two, three, four and five pulses is shown sequentially with the damage from a single pulse shown at the top and at the bottom the damage after five pulses delivered to the same target zone. It can be seen that after five pulses are delivered the target zone approximately 50% of the area has still not been affected.

When the target is a pigmented epithelial cell layer the result will be that a portion of the cells will not receive the full radiant intensity, and even if the energy profile varies slightly with each pulse, applying more pulses to the same area will not greatly improve the coverage.

Figure 6:
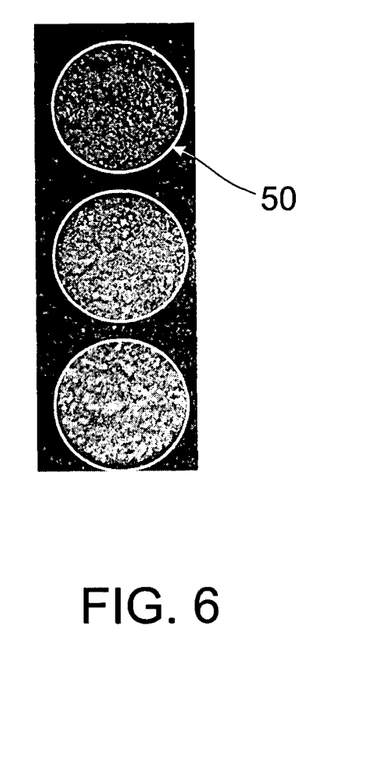
FIG. 6 shows the energy distribution profile of the same laser after passing through a uniform irradiance module.

FIG. 6 shows the same result for one, two and three pulses after the laser treatment beam has been passed through the uniform irradiance module 3 and the beam delivery and viewing module 4. Again the target treatment zone is shown by circle 50. The top image is the damage caused by a single pulse. The second image shows the damage caused by three pulses delivered to the same target area at a high repetition rate but without vibration of the optical fibre. The bottom image is the damage caused by five pulses delivered to the same target zone with lower repetition rate and vibration of the optical fibre, showing that almost 100% of the treatment zone has been affected. The shots are manually controlled to ensure the repetition rate is low compared to the rate of vibration of the fibre.

Figure 7:
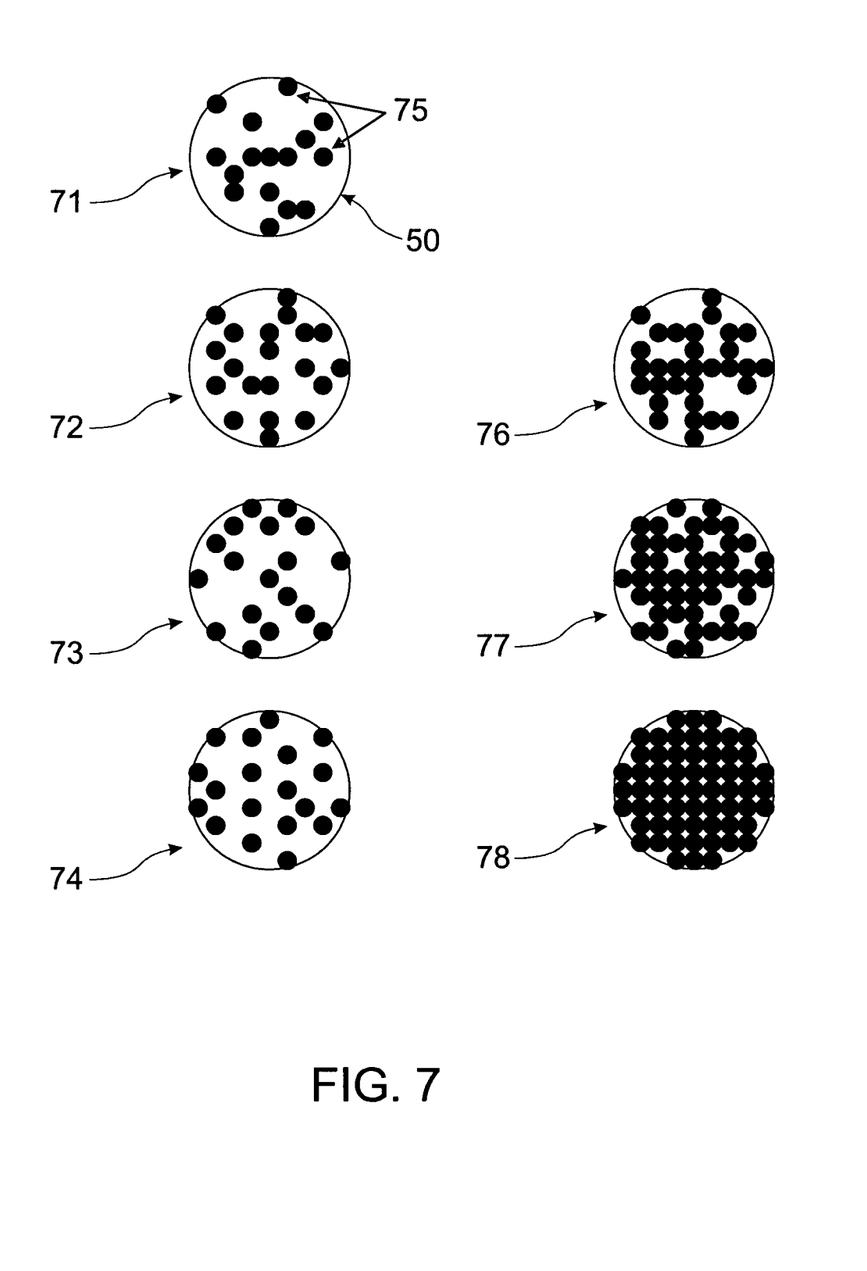
FIG. 7 is a diagrammatic representation of the effect of firing multiple laser pulses with different speckle patterns onto the same target zone.

FIG. 7 is a diagrammatic representation of multiple laser pulses (71-74) with different speckle patterns being fired at a common target treatment zone 50 to further explain the image in FIG. 6. The speckle pattern peaks are depicted by dark spots 75, The cumulative effect of laser pulses 71 and 72 is shown at 76. The addition of laser pulse 73 results in the image 77 and the addition of laser pulse 74 results in image 78. It can be seen that the cumulative effect of different speckle pattern peaks on each successive pulse results in increasing coverage of the treatment zone, allowing the degree of coverage to be determined by the number of pulses delivered to the target treatment zone.

When this technique is applied to the treatment of pigmented cell layers such as the RPE of the human eye the pulse separation can be chosen so that there is no additive effect between pulses, so peaks in the speckle pattern that occur in the same position on subsequent pulses do not cause an increased treatment effect in those areas. For example, if a 3 ns laser pulse duration and 1 kHz pulse repetition rate is used, no additive thermal effect will occur with multiple pulses. If a passively Q-switched, flashlamp pumped laser is used as shown in FIG. 2, multiple pulses may be obtained by increasing the energy which is discharged through the flashlamp, or by charging multiple discharge capacitors and then discharging them individually through the flashlamp by means of an electronic switching and control system.

By using pulse durations within the 50 ps to 500 ns range RPE cells can be killed or altered by explosive bubble formation around melanosomes within the cells and thermal effects are fully contained within the cells, preventing collateral damage to surrounding cells or structures. At pulse lengths less than about 50 picoseconds the laser pulse is so short that all the pulse energy is deposited in less than the time required for an acoustic wave to traverse the optical path causing mechanical damage such as photodisruption along the beam path. At pulse durations longer than about 500 nanoseconds it may not be possible to fully contain the thermal effects within the cells, particularly where melanosomes are congregated around the interface with the photoreceptors, which could result in permanent damage to the RPE/photoreceptor interface.

The retinal rejuvenation laser described may be used to improve the function of the retina of the human eye in the following manner. A variety of diagnostic techniques can be applied, depending on the retinal disease that is being treated, to select patients that are suitable for the laser treatment and to determine the laser treatment areas. For example, for diabetic macular edema it is useful to use scanning laser ophthalmoscopy and optical coherence tomography to identify the region of edema, while for early AMD dark adaptation tests and autofluorescence imaging can be used to identify compromised retinal function.

As this technique relies on the migration and division of RPE cells it is important to treat areas where RPE cells are healthy, rather than targeting areas where poor retinal function is identified. For example, if autofluorescence imaging identified an area of hyperfluorescence, indicating compromised RPE function, laser treatment would be carried out on the periphery of the area, rather than the center.

A 1× Mainster Retinal Contact Lens, or similar, would then be applied to the patients eye. An energy of approximately 0.1 mJ would be selected and a retinal treatment spot size of approximately 400 micron selected. The laser would be fired around the treatment area, with the treatment spots spaced apart by approximately half a spot diameter. Energy can be incrementally titrated to just below the visible bubble formation threshold. The number of laser pulses delivered to each target treatment zone can be selected to provide the best therapeutic outcomes and optimum wound healing response.

The inventors envisage that the retinal rejuvenation laser will be useful for a wide range of procedures. The foregoing description is offered as an example of the use of the laser and is not meant to suggest that the use of the laser is limited to this procedure. Persons skilled in the field will be aware of specific optical elements that may be substituted for one or more of the elements described for the preferred embodiment without departing from the spirit and scope of the invention. Throughout the specification the aim has been to describe the invention without limiting the invention to any one particular combination of preferred features or embodiment.

The invention claimed is:

1. A laser treatment device for improving the function of the retina of a human eye by speckle pattern irradiation through the cornea of the eye to the retinal pigmented epithelium, comprising: a laser module producing a laser pulse or sequence of laser pulses each having: a pulse duration in the range of 50 ps to 500 ns; a wavelength in the range 500 nm to 900 nm; and a pulse energy in the range 10 μJ to 10 mJ; a uniform irradiance module that modifies an output beam profile of each pulse of the laser module to have a different granular spatial distribution of laser energy in order to optimize the therapeutic benefit provided by the laser treatment device; and a beam delivery and viewing module that delivers the laser pulse or pulses to the retinal pigmented epithelium with a radiant exposure in the range of 8 mJ/cm$^2$ to 8000 mJ/cm$^2$ per pulse.

2. The laser treatment device of claim 1 wherein the laser module produces from 1 to 5 laser pulses.

3. The laser treatment device of claim 1 wherein the laser module produces a single pulse.

4. The laser treatment device of claim 1 wherein pulse duration is around 3 ns.

5. The laser treatment device of claim 1 wherein the laser module comprises a Q-switched solid state laser.

6. The laser treatment device of claim 1 further comprising a frequency doubling crystal.

7. The laser treatment device of claim 1 wherein the wavelength is about 532 nm.

8. The laser treatment device of claim 1 producing a radiant exposure in the range 20 mJ/cm$^2$ to 300 mJ/cm$^2$ per pulse.

9. The laser treatment device of claim 1 wherein the laser module contains an optical attenuator.

10. The laser treatment device of claim 9 wherein the optical attenuator comprises a half wave plate and a polarizing optic.

11. The laser treatment device of claim 1 wherein the uniform irradiance module comprises an optical fibre.

12. The laser treatment device of claim 11 wherein the optical fibre has a numerical aperture in the range 0.1 to 0.35.

13. The laser treatment device of claim 11 wherein the uniform irradiance module further comprises an optical fibre vibrator.

14. The laser treatment device of claim 1 wherein the uniform irradiance module further comprises a motor with an offset load shaft that mechanically vibrates the optical fibre.

15. The laser treatment device of claim 1 wherein the beam delivery and viewing module includes an optical zoom module.

16. A method of laser treatment of the retina of a human eye by speckle pattern irradiation through the cornea of the eye to the retinal pigmented epithelium, the method comprising: producing a laser pulse or sequence of laser pulses each having: a pulse duration in the range of 50 ps to 500 ns; a wavelength in the range 500 nm to 900 nm; a pulse energy in the range 10 μJ to 10 mJ; modifying an output beam profile of each laser pulse to have a different granular spatial distribution of laser energy in order to optimize the therapeutic benefit provided by the laser treatment; and delivering the laser pulse or pulses to the retinal pigmented epithelium with a radiant exposure in the range of 8 mJ/cm$^2$ to 8000 mJ/cm$^2$ per pulse.

17. The method of claim 16, wherein the method includes the step of selecting the number of pulses delivered in order to achieve a desired coverage of a target treatment zone.

18. The method of claim 16, wherein a single laser pulse is produced and delivered.

\* \* \* \* \*